United States Patent [19]

Manabe et al.

[11] Patent Number: 5,087,704
[45] Date of Patent: Feb. 11, 1992

[54] CYANINE COMPOUNDS

[75] Inventors: Osamu Manabe, Osaka; Shigeo Fujita, Kawachinagano; Shizuo Iwata, Kishiwada; Morihiro Kamiyama, Ibaraki, all of Japan

[73] Assignee: Asahi Chemical Co., Ltd., Osaka, Japan

[21] Appl. No.: 474,094

[22] PCT Filed: Sep. 6, 1989

[86] PCT No.: PCT/JP89/00918
§ 371 Date: May 4, 1990
§ 102(e) Date: May 4, 1990

[87] PCT Pub. No.: WO90/02777
PCT Pub. Date: Mar. 22, 1990

[30] Foreign Application Priority Data
Sep. 9, 1988 [JP] Japan ................. 63-227091

[51] Int. Cl.⁵ ............. C07D 209/56; C07D 491/044; C07D 491/056
[52] U.S. Cl. ..................... 548/427; 548/430; 548/405
[58] Field of Search ............. 548/427, 430, 405

[56] References Cited

U.S. PATENT DOCUMENTS

| | | | |
|---|---|---|---|
| 3,592,653 | 7/1971 | Fumia et al. | 96/101 |
| 3,916,069 | 10/1975 | Tiers et al. | 428/411 |
| 3,974,147 | 8/1976 | Tiers et al. | 260/240 |
| 4,025,347 | 5/1977 | Beretta et al. | 96/101 |
| 4,600,625 | 7/1986 | Abet et al. | 428/167 |
| 4,735,839 | 4/1988 | Sato et al. | 423/64 |
| 4,847,385 | 7/1989 | Kusakata et al. | 548/455 |

FOREIGN PATENT DOCUMENTS 59-85791 5/1984 Japan.
60-226035 11/1985 Japan.
62-232461 10/1987 Japan.

*Primary Examiner*—Mary C. Lee
*Assistant Examiner*—Joseph K. McKane
*Attorney, Agent, or Firm*—Armstrong, Nikaido, Marmelstein, Kubovcik & Murray

[57] ABSTRACT

The present invention provides a cyanine compound represented by the formula $$R^1HC\underset{Y}{\overset{X}{\diagup}}\!\!\!\diagdown\!\!\!\underset{}{\overset{CH_3\ \ CH_3}{\diagup\diagdown}}(CH=CH)_{\overline{n}}$$
$$\underset{R^2}{\overset{N_\oplus}{|}}$$

$$-CH=\underset{\underset{R^2}{|}}{\overset{CH_3\ CH_3}{\diagdown\diagup}}\!\!\!\underset{N}{\diagdown}\!\!\!\underset{Y}{\diagup\diagdown}\!\!\!\overset{X}{\diagdown}CHR^1.Z^\ominus$$

wherein $R^1$ is a hydrogen atom or a lower alkyl group, $R^2$ is an optionally substituted lower alkyl group, X and Y are the same or different and each represent a methylene group or an oxygen atom, Z is an acidic residue, and n is 2 or 3. This cyanine compound is suitable for use as a near infrared light-absorbing organic dye useful as an optical disc recording medium for semiconductor laser recording.

6 Claims, No Drawings

CYANINE COMPOUNDS

FIELD OF THE INVENTION

The present invention relates to novel cyanine compounds.

PRIOR ART

Prevalently used among inorganic recording media for semiconductor laser recording are those containing a predominant amount of tellurium for forming a recording layer. However, tellurium-type materials have the drawbacks of being toxic, low in corrosion resistance, expensive and unfit to densify. Research is under way to develop an organic dye which can replace the inorganic tellurium-type materials.

Given below are important characteristics required of organic dyes used as recording media:

(1) properties of markedly absorbing near infrared light at approximately 700 to 900 nm and undergoing fusion, sublimation, decomposition and like changes by the action of resulting heat energy;
(2) desirable ability of the dye layer to reflect intensely the light for detection of signals in reproduction;
(3) good solubility in a solvent because the recording layer is formed by wet coating method; and
(4) an ability to give records having a highly stable shape retention and an excellent retentivity (assuring a retention for 10 years or more) and unlikely to deteriorate in properties on exposure to light in reproduction.

While organic dyes are advantageous in being low in toxicity, high in corrosion resistance, inexpensive and fit to densify as compared with the foregoing inorganic materials, an organic dye remains to be developed which has the characteristics described above in items (2) and (3) among those in items (1) to (4).

DISCLOSURE OF THE INVENTION

An object of the present invention is to provide a cyanine compound suitable for use as an organic near infrared light-absorbing dye for an optical disc recording medium adapted for semiconductor laser recording.

Another object of the present invention is to provide a cyanine compound having the foregoing characteristics (1) to (4) required of an organic near infrared light-absorbing dye which is useful as an optical disc recording medium adapted for semiconductor laser recording.

A further object of the invention is to provide a cyanine compound having a high reflectivity comparable to that of inorganic tellurium-type materials.

A still further object of the invention is to provide a cyanine compound excellent in solubility in a solvent.

The cyanine compounds of the present invention are novel compounds undisclosed in literature and represented by the following formula (1)

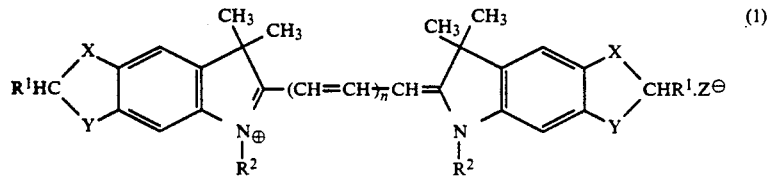

wherein $R^1$ is a hydrogen atom or a lower alkyl group, $R^2$ is an optionally substituted lower alkyl group, X and Y are the same or different and each represent a methylene group or an oxygen atom, Z is an acidic residue, and n is 2 or 3.

Shown below are specific examples of the groups represented by $R^1$, $R^2$ and Z in the formula (1).

Examples of the lower alkyl group are methyl, ethyl, n-propyl, isopropyl, n-butyl, isobutyl, tert-butyl, n-hexyl, n-heptyl, n-octyl and like $C_1$-$C_8$ alkyl groups.

Illustrative of the substituents for the lower alkyl group are $C_1$-$C_8$ alkoxy, hydroxyl, sulfonic acid group, carboxy, ($C_1$-$C_8$ alkyl)amino, phenylsulfonyl amino, p-methylphenylsulfonyl amino, acetoxy, ($C_1$-$C_3$ alkoxy)carbonyl, ($C_1$-$C_3$ alkoxy)($C_1$-$C_3$ alkoxy)carbonyl and the like. Specific examples of the lower alkyl group having such substituents are methoxymethyl, ethoxymethyl, 2-methoxyethyl, 2-ethoxyethyl, 2-(n-butoxy)ethyl, n-butoxymethyl, 2-hydroxyethyl, a group $-(CH_2)_m-SO_3Na$ (wherein m is an integer of 1 to 8), methylaminomethyl, dimethylaminomethyl, 2-(p-methylphenylsufonylamino)ethyl, acetoxymethyl, 2-acetoxyethyl, methoxycarbonylmethyl, methoxymethoxymethyl, 2-ethoxyethoxyethyl and the like.

Examples of the group Z are halogen, alkyl sulfate residue, arylsulfonate residue, perchlorate residue, tetrafluoroborate residue, arylcarboxylic acid residue and the like. When Z is a halogen atom, examples of $Z^-$ are $Cl^-$, $Br^-$, $I^-$, $F^-$ and the like. When Z is an alkyl sulfate residue, examples of $Z^-$ are $CH_3SO_4^-$, $C_2H_5SO_4^-$, $n-C_3H_7SO_4^-$, $n-C_4H_9SO_4^-$ and the like. When Z is an arylsufonate residue, examples of $Z^-$ are

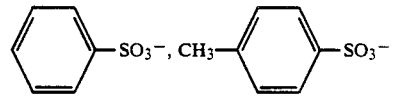

and the like. When Z is a perchlorate residue, examples of $Z^-$ are $ClO_4^-$ and the like. When Z is a tetrafluoroborate residue, examples of $Z^-$ include $BF_4^-$ and the like. When Z is an arylcarboxylic acid residue, examples of $Z^-$ include a group

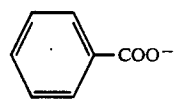

and the like.

The compound of the formula (1) according to the present invention can be prepared by various processes, for example can be easily prepared by the following process.

Stated more specifically, the compound of the present invention can be prepared by subjecting to condensation reaction an indolenium salt represented by the formula

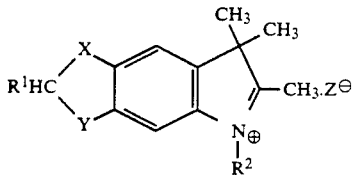

(2)

wherein R¹, R², X, Y and Z are as defined above and a known compound represented by the formula

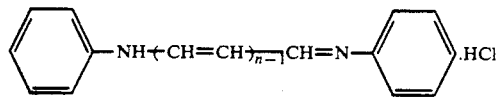

(3)

wherein n is as defined above.

The condensation reaction can be conducted in an anhydrous organic acid in the presence of a fatty acid salt. Examples of such fatty acid salt are sodium acetate, potassium acetate, calcium acetate, sodium propionate, potassium propionate and the like. The fatty acid salt is used in an amount of about 0.5 to about 3 moles, preferably about 1 to about 2 moles, per mole of the compound of the formula (2). Representative of the anhydrous organic acid are acetic anhydride, propionic anhydride, butyric anhydride, γ-butyrolactone and the like. The amount of the anhydrous organic acid to be used is usually about 10 to about 100 moles, preferably about 20 to about 50 moles, per mole of the compound of the formula (2). The proportions of the compounds of the formulae (2) and (3) are about 0.2 to about 1.5 moles, preferably about 0.4 to about 0.7 mole, of the latter per mole of the former. The reaction smoothly proceeds at a temperature of about 50° to about 150° C., preferably about 70° to about 140° C. and is completed usually in about 10 to about 60 minutes.

The indolenium salts of the formula (2) (the compounds of the formulas (2a) and (2b)) are novel compounds undisclosed in literature and can be prepared, for example, by the following process:

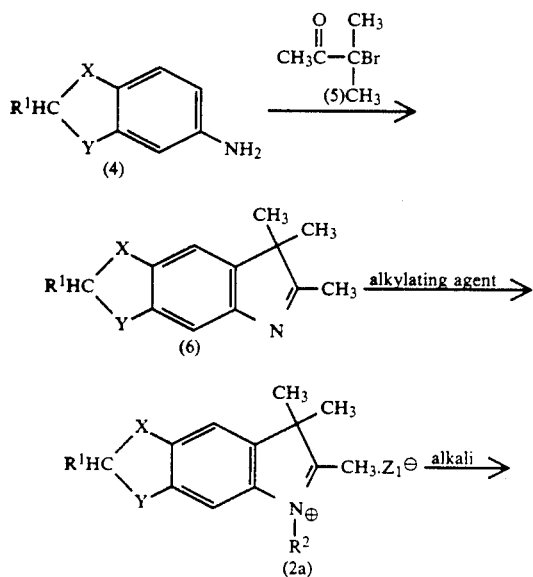

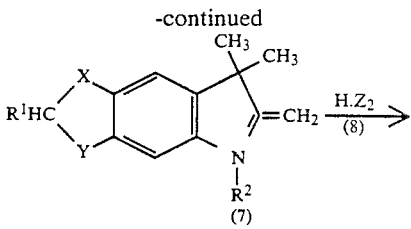

(7)

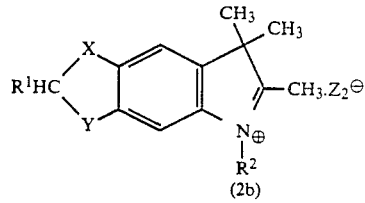

(2b)

wherein $Z_1$ is an acidic residue other than perchlorate residue and tetrafluoroborate residue, $Z_2$ is a perchlorate residue or a tetrafluoroborate residue, and R¹, R², X and Y are as defined above.

The reaction between the conventional aniline derivative of the formula (4) and the conventional 3-bromo-3-methyl-2-butanone of the formula (5) is conducted in the presence of an acid scavenger. Examples of the acid scavenger are pyridine, triethylamine, tri-n-propylamine, tri-n-butylamine and like tertiary amines; sodium carbonate, potassium carbonate, calcium carbonate and like alkali metal salts of carbonic acids; sodium acetate, potassium acetate, calcium acetate and like alkali metal salts of acetic acids; etc. Generally the acid scavenger is used in an amount of about 0.3 to about 5 moles, preferably about 0.5 to about 1.5 moles, per mole of the compound of the formula (4). The suitable proportions of the compounds of the formulas (4) and (5) are about 0.3 to about 5 moles, preferably about 0.5 to about 1.5 moles, of the latter per mole of the former. The reaction is conducted usually at a temperature in the range of from ambient temperature to about 200° C., preferably about 50° to about 150° C. and is completed usually in several hours to about 25 hours, preferably about 5 to about 15 hours.

The compound of the formula (2a) can be prepared by causing an alkylating agent to act on the indolenine derivative of the formula (6). Useful as such alkylating agent are, for example, alkyl toluenesulfonates such as methyl toluenesulfonate, ethyl toluenesulfonate, n-propyl toluenesulfonate, isopropyl toluenesulfonate, n-butyl toluenesulfonate and the like; halogenated alkyls such as ethyl bromide, n-propyl bromide, n-butyl bromide, ethyl iodide, n-propyl iodide, n-propyl chloride, n-butyl chloride and the like; dialkyl sulfates such as dimethyl sulfate, diethyl sulfate and the like; a mixture of acids and epoxy compounds (e.g. a mixture of hydrochloric acid, sulfuric acid or like inorganic acid, acetic acid, propionic acid or like organic acid and ethylene oxide, propylene oxide or the like); alkyl sultones such as methyl sultone, ethyl sultone, propyl sultone, butyl sultone and the like; etc. The alkylating agent is used in an amount of usually about 0.3 to about 5 moles, preferably about 0.5 to about 2 moles, per mole of the compound (6). The reaction is carried out in the presence or the absence of a solvent. Useful solvents include, for example, toluene, xylene and like alkyl benzenes, n-octane, n-decane, cyclohexane, decalin and like aliphatic hydrocarbons, benzene, naphthalin, tetralin and like aromatic hydrocarbons, trichloroethane, tetrachloroethane, chlorobenzene, dichlorobenzene and like halogenated hydrocarbons, etc. The reaction is effected usually at a temperature in the range of from room temperature to about 200° C., preferably about 50° to about 150° C. and is completed in usually about 2 to about 30 hours, preferably about 5 to about 25 hours.

The compound of the formula (7) can be produced by treating the compound (2a) with alkali in an appropriate solvent such as water. The alkali to be used can be any of those conventionally used, such as sodium hydroxide, potassium hydroxide and the like. The amount of the alkali to be used is usually about 1 to about 20 moles, preferably about 1 to about 5 moles, per mole of the compound (2a). The solvent is usually used in an amount of about 2 to about 100 moles, preferably about 2 to about 20 moles, per mole of the compound (2a). The reaction is conducted usually at 0° to about 150° C., preferably 0° to about 100° C. and is completed generally in tens of minutes to about 10 hours, preferably about 1 to about 5 hours.

The compound of the formula (2b) is prepared by reacting the compound (7) with the compound of the formula (8) in a suitable solvent such as methanol, ethanol, n-propyl alcohol, isopropyl alcohol, n-butanol, isobutyl alcohol, tert-butyl alcohol or like alcohols, benzene, toluene, xylene, n-octane, n-decane, cyclohexane, decalin, trichloroethane, tetrachloroethane, chlorobenzene, dichlorobenzene or like hydrocarbons, etc. The proportions of the compounds of the formulas (7) and (8) are usually about 0.3 to about 10 moles, preferably about 0.5 to about 3 moles, of the latter per mole of the former. The reaction is performed usually at 0° to about 70° C. and is completed in about 10 minutes to about 3 hours.

The thus obtained compounds of the present invention can be readily isolated from the reaction mixture and purified by common purification means such as recrystallization, column chromatography or the like.

The compound of the formula (1) according to the present invention exhibits a good solubility in an organic solvent such as methanol, ethanol, n-propyl alcohol, isopropyl alcohol, n-butanol, isobutanol, tert-butanol or like alcohol, dichloromethane, dichloroethane or like aliphatic halogenated hydrocarbon or the like. The compounds of the invention have an absorption maximum at about 670 to about 830 nm and has a high molar absorptivity. Further, when used as an optical disk recording medium for semiconductor laser recording, the compound displays a remarkably high optical reflectivity on irradiation of laser beam for reproduction and is therefore especially valuable for use. The compounds of the invention are also capable of achieving a marked absorption as compared with usual dyes and is therefore suitable for use as a dye for filters, or as a photosensitive material or a sensitizing dye for photosensitive materials in copying and printing. Moreover, the compounds of the invention are usable as a medical diagnosis for examining the function of livers, as a dye for Langmuir-Blodgett film, etc.

EXAMPLES

Given below are a reference example illustrating the preparation of the compound of the formula (2) and preparation examples illustrating the preparation of the compounds of the invention.

REFERENCE EXAMPLE

A mixture of 20.57 g of 3,4-methylenedioxyaniline, 24.76 g of 3-bromo-3-methyl-2-butanone and 75 ml of pyridine was reacted at 50° to 55° C. for 5 hours. Then the reaction mixture was refluxed for 10 hours. After completion of the reaction, the reaction mixture was poured into 100 ml of water and extracted with 50 ml of dichloromethane. After removal of the solvent, the residue was subjected to vacuum distillation, giving 11.64 g of 2,3,3-trimethyl-5,6-methylenedioxyindolenine.

Boiling point:134° to 136° C./4 to 5 mmHg

A 10.16 g portion of 2,3,3-trimethyl 5,6-methylenedioxyindolenine obtained above, 13.67 g of n-butyl p-toluenesulfonate and 40 ml of chlorobenzene were mixed together and reacted with refluxing for 20 hours. After the reaction, 1-(n-butyl)-2,3,3-trimethyl-5,6-methylenedioxyindolenium toluenesulfonate was extracted using 60 ml of water.

To the extract was added 20 g of 20% NaOH and the mixture was reacted at 70° C. for 3 hours, followed by extraction with 30 ml of toluene. After toluene was distilled off, the residue was subjected to vacuum distillation, giving 5.25 g of 1-(n-butyl)-3,3-dimethyl-2-methylene-5,6-methylenedioxyindoline.

Boiling point:162° to 164° C./5 to 6 mmHg

A 3.24 g quantity of 70% HClO4 was added to a mixture of 5.00 g of 1-(n-butyl)-3,3-dimethyl-2-methylene5,6-methylenedioxyindoline obtained above and 100 ml of isopropyl alcohol at a temperature up to 20° C. The resulting mixture was stirred at room temperature for 1 hour and then cooled to not more than 5° C. The precipitated crystals were separated by filtration, washed and dried, giving 6.94 g of 1-(n-butyl)-2,3,3-trimethyl-5,6-methylenedioxyindolenium perchlorate.

Melting point:147.0° to 150.0° C.

PREPARATION EXAMPLE 1

To 20 ml of acetic anhydride were added 1.45 g of the compound of the formula (2) (wherein $R^1$=H, $R^2$=n-butyl, X=O, Y=O, $Z^-$=$ClO_4^-$), 0.52 g of β-anilino acroleinanile hydrochloride and 0.68 g of potassium acetate. The mixture was refluxed for 10 minutes and then poured into 100 ml of water. The precipitated crystals were separated by filtration, washed with water and recrystallized from methanol, giving 1.05 g of the compound of the formula (1) (wherein $R^1$=H, $R^2$=n-butyl, X=O, Y=O, $Z^-$=$ClO_4^-$, n=2). Given below are the melting point, wavelength at maximum absorption (λmax) and molar absorptivity (ε) of the compound obtained above.

Melting point:242.0° to 243.0° C.
λmax:696 nm (methanol)
ε:1.76×10$^5$ cm$^{-1}$

PREPARATION EXAMPLE 2

To 100 ml of acetic anhydride were added 9.34 g of the compound of the formula (2) (wherein $R^1$=H, $R^2$=ethyl, X=O, Y=O, $Z^-$=$I^-$), 3.36 g of β-anilinoacroleinanile hydrochloride and 4.30 g of potassium acetate. The mixture was refluxed for 10 minutes and then poured into 600 ml of water. The precipitated crystals were separated by filtration, washed with water and recrystallized from methanol, giving 5.20 g of the compound of the formula (1) (wherein $R^1$=H, $R^2$=ethyl, X=O, Y=O, $Z^-$=$I^-$, n=2).

The wavelength at maximum absorption (λmax) of the obtained compound was 694 nm (methanol).

PREPARATION EXAMPLE 3

To 100 ml of acetic anhydride were added 9.41 g of the compound of the formula (2) (wherein $R^1$=H, $R^2$=2-methoxyethyl, X=O, Y=O, $Z^-$=$ClO_4^-$), 3.74 g of glutaconic aldehyde dianilide hydrochloride and 4.30 g of potassium acetate. The mixture was refluxed for 10 minutes and poured into 600 ml of water. The precipitated crystals were separated by filtration, washed with water and recrystallized from methanol, giving 6.00 g of the compound of the formula (1) (wherein $R^1$=H, $R^2$=2-methoxyethyl, X=O, Y=O, $Z^-$=$ClO_4^-$, n=3).

The wavelength at maximum absorption (λmax) of the thus obtained compound was 793 nm (methanol).

PREPARATION EXAMPLE 4

A 2.09 g quantity of the compound of the formula (1) (wherein $R^1$=methyl, $R^2$=n-butyl, X=O, Y=methylene, $Z^-$=$ClO_4^-$, n=2) was prepared in the same manner as in Preparation Example 1 using 5.34 g of the compound of the formula (2) (wherein $R^1$=methyl, $R^2$=n-butyl, X=O, Y=methylene, $Z^-$=$ClO_4^-$). The melting point, wavelength at maximum absorption (λmax) and molar absorptivity (ε) of the compound obtained above were as follows.

Melting point:227° to 228° C.
λmax:695 nm (diacetone alcohol)
ε:1.94×10⁵ cm⁻¹

PREPARATION EXAMPLE 5

The same procedure as in Preparation Example 1 was repeated using 5.34 g of the compound of the formula (2) (wherein $R^1$=methyl, $R^2$=n-butyl, X=methylene, Y=O, $Z^-$=$ClO_4^-$) giving 2.76 g of the compound of the formula (1) (wherein $R^1$=methyl, $R^2$=n-butyl, X=methylene, Y=O, $Z^-$=$ClO_4^-$, n=2). Given below are the melting point, wavelength at maximum absorption (λmax) and molar absorptivity (ε) of the obtained compound.

Melting point:215° to 217° C.
λmax:688 nm (diacetone alcohol)
ε:1.90×10⁵ cm⁻¹

PREPARATION EXAMPLE 6

A 2.20 g quantity of the compound of the formula (1) (wherein $R^1$=H, $R^2$=n-butyl, X=methylene, Y=methylene, $Z^-$=$ClO_4^-$, n=2) was produced by the same procedure as in Preparation Example 1 using 4.00 g of the compound of the formula (2) (wherein $R^1$=H, $R^2$=n-butyl, X=methylene, Y=methylene, $Z^-$=$ClO_4^-$). The melting point, wavelength at maximum absorption (λmax) and molar absorptivity (ε) of the thus obtained compound were as follows.

Melting point:163° to 165° C.
λmax:670 nm (diacetone alcohol)
ε:2.24×10⁵ cm⁻¹

PREPARATION EXAMPLE 7

The compound of the formula (1) (wherein $R^1$=H, $R^2$=2-ethoxyethyl, X=methylene, Y=methylene, $Z^-$=$ClO_4^-$, n=2) was prepared in the same manner as in Preparation Example 1 using the compound of the formula (2) (wherein $R^1$=H, $R^2$=2-ethoxyethyl, X=methylene, Y=methylene, $Z^-$=$ClO_4^-$). The wavelength at maximum absorption (λmax) and molar absorptivity (ε) of the obtained compound were as follows.

λmax:672 nm (diacetone alcohol)
ε:2.20×10⁵ cm⁻¹

PREPARATION EXAMPLE 8

The same procedure as in Preparation Example 1 was repeated using the compound of the formula (2) (wherein $R^1$=H, $R^2$=2-acetoxyethyl, X=methylene, Y=methylene, $Z^-$=$BF_4^-$), giving the compound of the formula (1) (wherein $R^1$=H, $R^2$=2-acetoxyethyl, X=methylene, Y=methylene, $Z^-$=$BF_4^-$, n=3). The obtained compound had the following wavelength at maximum absorption (λmax) and molar absorptivity (ε).

λmax:768 nm
ε:2.28×10⁵ cm⁻¹

PREPARATION EXAMPLE 9

The compound of the formula (1) (wherein $R^1$=H, $R^2$=2-methoxyethyl, X=methylene, Y=methylene, $Z^-$=$I^-$, n=3) was prepared in the same manner as in Preparation Example 1 using the compound of the formula (2) (wherein $R^1$=H, $R^2$=2-methoxyethyl, X=methylene, Y=methylene, $Z^-$=$I^-$). Given below are the wavelength at maximum absorption (λmax) and molar absorptivity (ε) of the thus obtained compound.

λmax:768 nm
ε:2.30×105 cm⁻¹

PREPARATION EXAMPLE 10

The same procedure as in Preparation Example 1 was repeated using the compound of the formula (2) (wherein $R^1$=H, $R^2$=2-hydroxyethyl, X=O, Y=O,

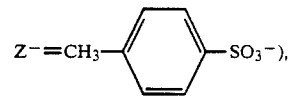

producing the compound of the formula (1) (wherein $R^1$=H, $R^2$=2-hydroxyethyl, X=O, Y=O,

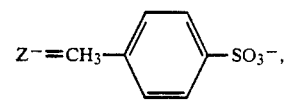

n=2). The wavelength at maximum absorption (λmax) and molar absorptivity (ε) of the obtained compound were as follows.

λmax:695 nm (diacetone alcohol)
ε:1.70×105 cm⁻¹

PREPARATION EXAMPLE 11

The compound of the formula (1) (wherein $R^1$=H, $R^2$=—$C_2H_4SO_3Na$, X=O, Y=O, $Z^-$=$Cl^-$, n=3) was produced by the same procedure as in Preparation Example 1 using the compound of the formula (2) (wherein $R^1$=H, $R^2$=—$C_2H_4SO_3Na$, X=O, Y=O, $Z^-$=$Cl^-$). Given below are the wavelength at maximum absorption (λmax) and molar absorptivity (ε) of the thus obtained compound.

λmax:790 nm (methanol)
ε:1.60×10⁵ cm−1

PREPARATION EXAMPLE 12

The same procedure as in Preparation Example 1 was repeated using the compound of the formula (2)

(wherein $R^1$=methyl, $R^2$=n-butyl, X=O, Y=methylene, $Z^-$=$C_2H_5SO_4^-$), giving the compound of the formula (1) (wherein $R^1$=methyl, $R^2$=n-butyl, X=O, Y=methylene, $Z^-$=$C_2H_5SO_4^-$, n=3). The obtained compound had the following wavelength at maximum absorption (λmax) and molar absorptivity (ε).

λmax:795 nm (methanol)
ε:$1.93 \times 10^5$ cm$^{-1}$

Test for reflectivity

Each of cyanine dyes as shown below in Table 1 was dissolved in diacetone alcohol to a concentration of 30 g/l. The solution was applied to an acrylic resin plate by a spin coater rotated at 150 rpm to form a layer having a thickness of 600 to 700 Å, followed by drying. The maximum reflectivity of the coated acrylic resin plate was measured on irradiation of light at a wave length of 770 to 800 nm onto the substrate. Table 1 shows the results.

TABLE 1

| Cyanine dye | Maximum reflectivity (%) |
|---|---|
| Dye of Prep. Ex. 1 | 45 |
| Dye of Prep. Ex. 2 | 45 |
| Dye of Prep. Ex. 4 | 39 |
| Dye of Prep. Ex. 5 | 40 |
| Dye of Prep. Ex. 7 | 42 |
| Dye of Prep. Ex. 10 | 45 |

Solubility in solvent

Each of cyanine dyes as shown below in Table 2 was dissolved in diacetone alcohol and the solubility was measured at room temperature. Table 2 shows the results.

TABLE 2

| Cyanine dye | Solubility (g/l) |
|---|---|
| Dye of Prep. Ex. 1 | At least 30 |
| Dye of Prep. Ex. 2 | 30 |
| Dye of Prep. Ex. 4 | At least 30 |
| Dye of Prep. Ex. 5 | At least 30 |
| Dye of Prep. Ex. 7 | 30 |
| Dye of Prep. Ex. 10 | At least 30 |

We claim:

1. A cyanine compound represented by the formula

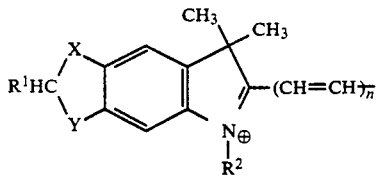

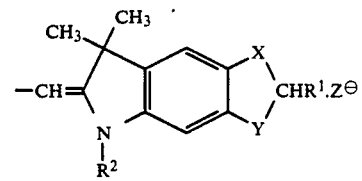

wherein
$R^1$ is a hydrogen atom or a lower alkyl group;
$R^2$ is a lower alkyl group which is unsubstituted or substituted with a substituent selected from $C_1$-$C_8$ alkoxy-, hydroxyl-, carboxyl-, ($C_1$-$C_8$ alkyl)amino-, phenylsulfonylamino-, p-methylphenylsulfonylamino-, acetoxy-, acetoxy-, ($C_1$-$C_3$ alkoxy)-carbonyl-, ($C_1$-$C_3$ alkoxy)($C_1$-$C_3$ alkoxy) carbonyl- and sulfonic acid group;
X and Y are the same or different and each represents a methylene group or an oxygen atom;
Z is an acidic residue, and
n is 2 or 3.

2. A compound according to claim 1 wherein X and Y are both a methylene group.

3. A compound according to claim 1 wherein X and Y are both an oxygen atom.

4. A compound according to claim 1 wherein X is a methylene group and Y is an oxygen atom.

5. A compound according to claim 1 wherein X is an oxygen atom and Y is a methylene group.

6. A compound according to claim 1 wherein Z is a halogen atom, an alkyl sulfate residue, an arylsulfonate residue, a perchlorate residue, a tetrafluoroborate residue or an arylcarboxylic acid residue.

* * * * *